US011056218B2

(12) United States Patent
Hu et al.

(10) Patent No.: US 11,056,218 B2
(45) Date of Patent: Jul. 6, 2021

(54) IDENTIFYING PERSONALIZED TIME-VARYING PREDICTIVE PATTERNS OF RISK FACTORS

(71) Applicant: International Business Machines Corporation, Armonk, NY (US)

(72) Inventors: Jianying Hu, Bronx, NY (US); Kenney Ng, Arlington, MA (US); Adam Perer, Pittsburgh, PA (US); Fei Wang, Ossining, NY (US); Yajuan Wang, White Plains, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 789 days.

(21) Appl. No.: 15/168,437

(22) Filed: May 31, 2016

(65) Prior Publication Data
US 2017/0344710 A1 Nov. 30, 2017

(51) Int. Cl.
*G16H 10/60* (2018.01)
*G16H 50/30* (2018.01)
*G16H 50/20* (2018.01)

(52) U.S. Cl.
CPC ............. *G16H 10/60* (2018.01); *G16H 50/20* (2018.01); *G16H 50/30* (2018.01)

(58) Field of Classification Search
CPC ......... G16H 10/60; G16H 50/30; G16H 50/20
See application file for complete search history.

(56) References Cited

U.S. PATENT DOCUMENTS

| 7,730,063 | B2 | 6/2010 | Eder | |
| 8,190,451 | B2* | 5/2012 | Lloyd | G06Q 50/22 705/3 |
| 8,990,135 | B2 | 3/2015 | Syed et al. | |
| 9,414,776 | B2* | 8/2016 | Sillay | A61B 5/11 |
| 2010/0070300 | A1* | 3/2010 | Anderson | G06Q 10/10 705/2 |
| 2014/0095186 | A1 | 4/2014 | Gotz et al. | |

(Continued)

OTHER PUBLICATIONS

Anonymous, OptCare—A system for personalizing clinical care pathways—IP.com No. IPCOM000244979D, Feb. 4, 2016; 13 pgs.

(Continued)

*Primary Examiner* — Eliza A Lam
(74) *Attorney, Agent, or Firm* — Cantor Colburn LLP; Kristofer Haggerty

(57) ABSTRACT

Aspects of the present invention include a method, system and computer program product. The method includes identifying, by a processor, a set of global risk factors for a target event using training patients, and providing, by the processor, a disease progression timeline with defined time stamps by aligning longitudinal data of the training patients based on the defined time stamp of risk targets. The method also includes positioning, by the processor, a target patient at one of the defined time stamps on the disease progression timeline, and identifying, by the processor, at least one of the training patients similar to the target patient with the same one of the defined time stamps on the disease progression timeline. The method further includes calculating, by the processor, a time-varying predictive pattern of at least a portion of the global set of risk factors for the target patient along the disease progression timeline.

20 Claims, 7 Drawing Sheets

(56) References Cited

U.S. PATENT DOCUMENTS

| | | | |
|---|---|---|---|
| 2015/0161331 A1* | 6/2015 | Oleynik | G06F 19/00 705/3 |
| 2015/0161346 A1 | 6/2015 | Hu et al. | |
| 2015/0213225 A1 | 7/2015 | Amarasingham et al. | |
| 2015/0220693 A1* | 8/2015 | Cadavid | A61B 5/4082 424/133.1 |
| 2015/0315652 A1 | 11/2015 | Rosenberg et al. | |
| 2016/0314256 A1* | 10/2016 | Su | G06F 19/00 |
| 2017/0262587 A1* | 9/2017 | Agarwal | G06F 19/325 |

OTHER PUBLICATIONS

Jiang, X., et al., "A patient-driven adaptive prediction technique to improve personalized risk estimation for clinical decision support" JAMIA, vol. 19, No. E1, ISSN: 1067-5027, (2012) pp. E137-E144.

* cited by examiner

IDENTIFYING PERSONALIZED TIME-VARYING PREDICTIVE PATTERNS OF RISK FACTORS

BACKGROUND

The present invention relates to the provision of human health care services, and more specifically, to a method, system and computer program product that identifies personalized time-varying predictive patterns of risk factors for humans having various diseases.

In the field of the provision of human health care services, a common set of risk factors may be determined and used to evaluate the disease status of various patients. However, these determined risk factors are typically generalized and are not patient-specific in nature. This is primarily because these risk factors are commonly based on a relatively general investigation of the population—that is, a "volume" approach instead of an individual-specific, more value-like approach to patient health care. Also, these determined risk factors usually do not reflect the time-varying physiopathology or functional change nature of a disease.

SUMMARY

According to one or more embodiments of the present invention, a computer-implemented method includes identifying, by a processor, a set of global risk factors for a target event using training patients, and providing, by the processor, a disease progression timeline with defined time stamps by aligning longitudinal data of the training patients based on the defined time stamp of risk targets. The computer-implemented method also includes positioning, by the processor, a target patient at one of the defined time stamps on the disease progression timeline, and identifying, by the processor, at least one of the training patients similar to the target patient with the same one of the defined time stamps on the disease progression timeline. The computer-implemented method further includes calculating, by the processor, a time-varying predictive pattern of at least a portion of the set of global risk factors for the target patient along the disease progression timeline.

According to another embodiment of the present invention, a system includes a processor in communication with one or more types of memory, the processor configured to identify a set of global risk factors for a target event using training patients, and provide a disease progression timeline with defined time stamps by aligning longitudinal data of the training patients based on the defined time stamp of risk targets. The processor is also configured to position a target patient at one of the defined time stamps on the disease progression timeline, and identify at least one of the training patients similar to the target patient with the same one of the defined time stamps on the disease progression timeline. The processor is further configured to calculate a time-varying predictive pattern of at least a portion of the set of global risk factors for the target patient along the disease progression timeline.

According to yet another embodiment of the present invention, a computer program product includes a non-transitory storage medium readable by a processing circuit and storing instructions for execution by the processing circuit for performing a method that includes identifying, by a processor, a set of global risk factors for a target event using training patients, and providing, by the processor, a disease progression timeline with defined time stamps by aligning longitudinal data of the training patients based on the defined time stamp of risk targets. The method also includes positioning, by the processor, a target patient at one of the defined time stamps on the disease progression timeline, and identifying, by the processor, at least one of the training patients similar to the target patient with the same one of the defined time stamps on the disease progression timeline. The method further includes calculating, by the processor, a time-varying predictive pattern of at least a portion of the set of global risk factors for the target patient along the disease progression timeline.

Additional features and advantages are realized through the techniques of the present invention. Other embodiments and aspects of the invention are described in detail herein and are considered a part of the claimed invention. For a better understanding of the invention with the advantages and the features, refer to the description and to the drawings.

BRIEF DESCRIPTION OF THE DRAWINGS

The subject matter which is regarded as the invention is particularly pointed out and distinctly claimed in the claims at the conclusion of the specification. The forgoing and other features, and advantages of the invention are apparent from the following detailed description taken in conjunction with the accompanying drawings in which:

DETAILED DESCRIPTION

Figure 1:
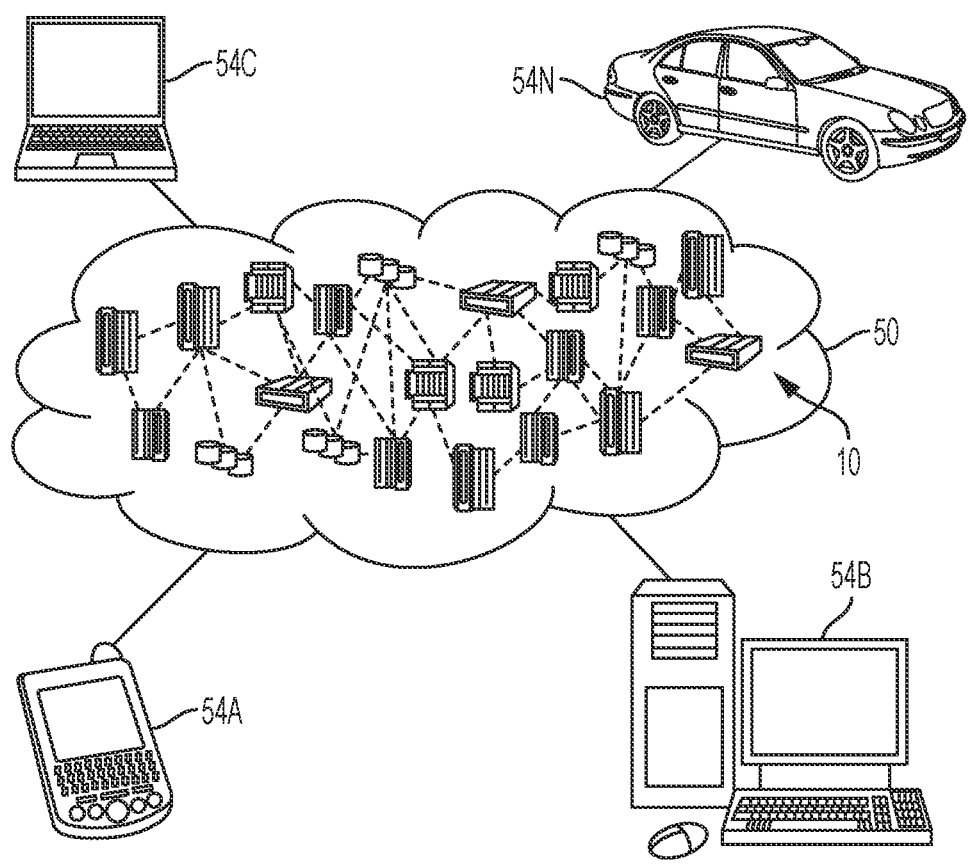
FIG. 1 depicts a cloud computing environment according to one or more embodiments of the present invention.

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Referring now to FIG. 1, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 1 are intended to be illustrative only and that computing nodes 10 and cloud computing environment 50 can communicate with any type of computerized device over any type of network and/or network addressable connection (e.g., using a web browser).

Figure 2:
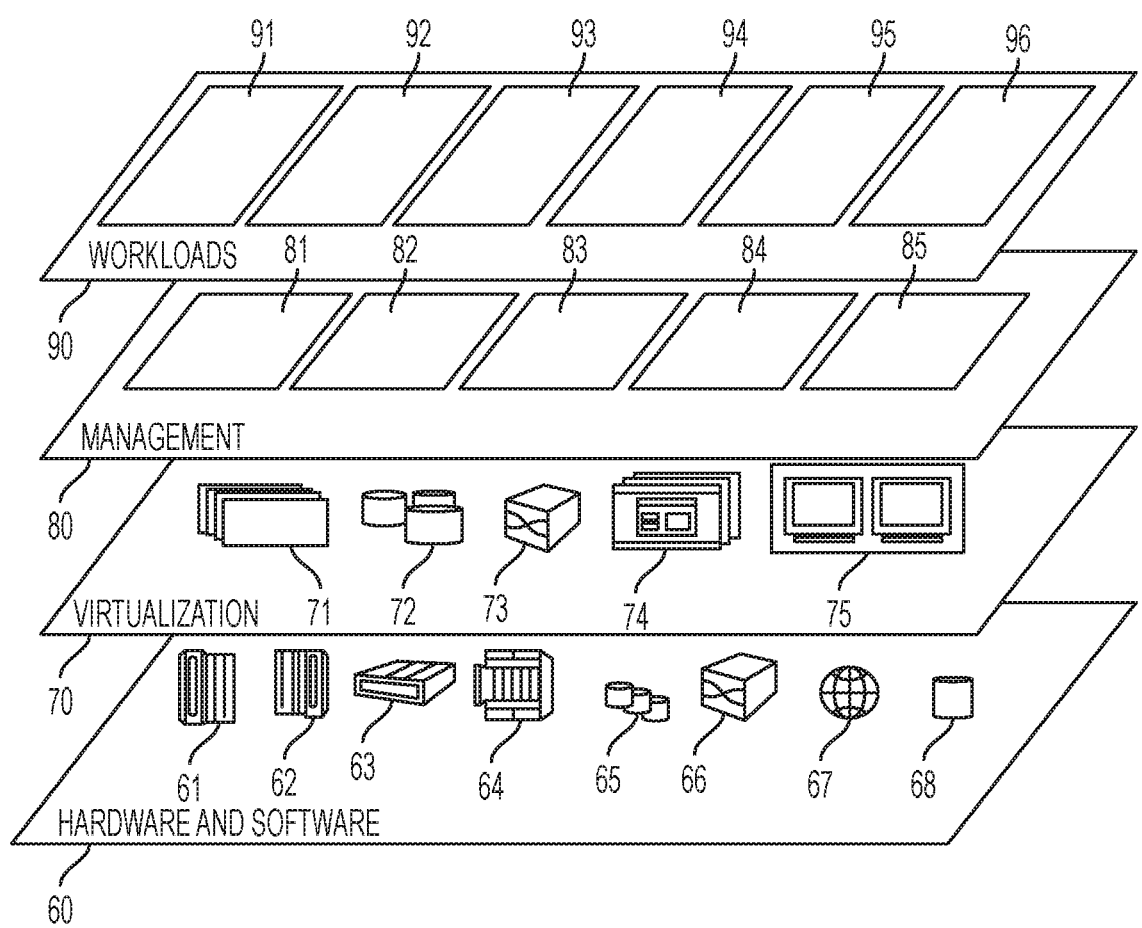
FIG. 2 depicts abstraction model layers according to one or more embodiments of the present invention.

Referring now to FIG. 2, a set of functional abstraction layers provided by cloud computing environment 50 (FIG. 1) is shown. It should be understood in advance that the components, layers, and functions shown in FIG. 2 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and a method 96 for identifying personalized time-varying predictive patterns of risk factors to one or more particular target events for a specific individual patient in accordance with one or more embodiments of the present invention.

Figure 3:
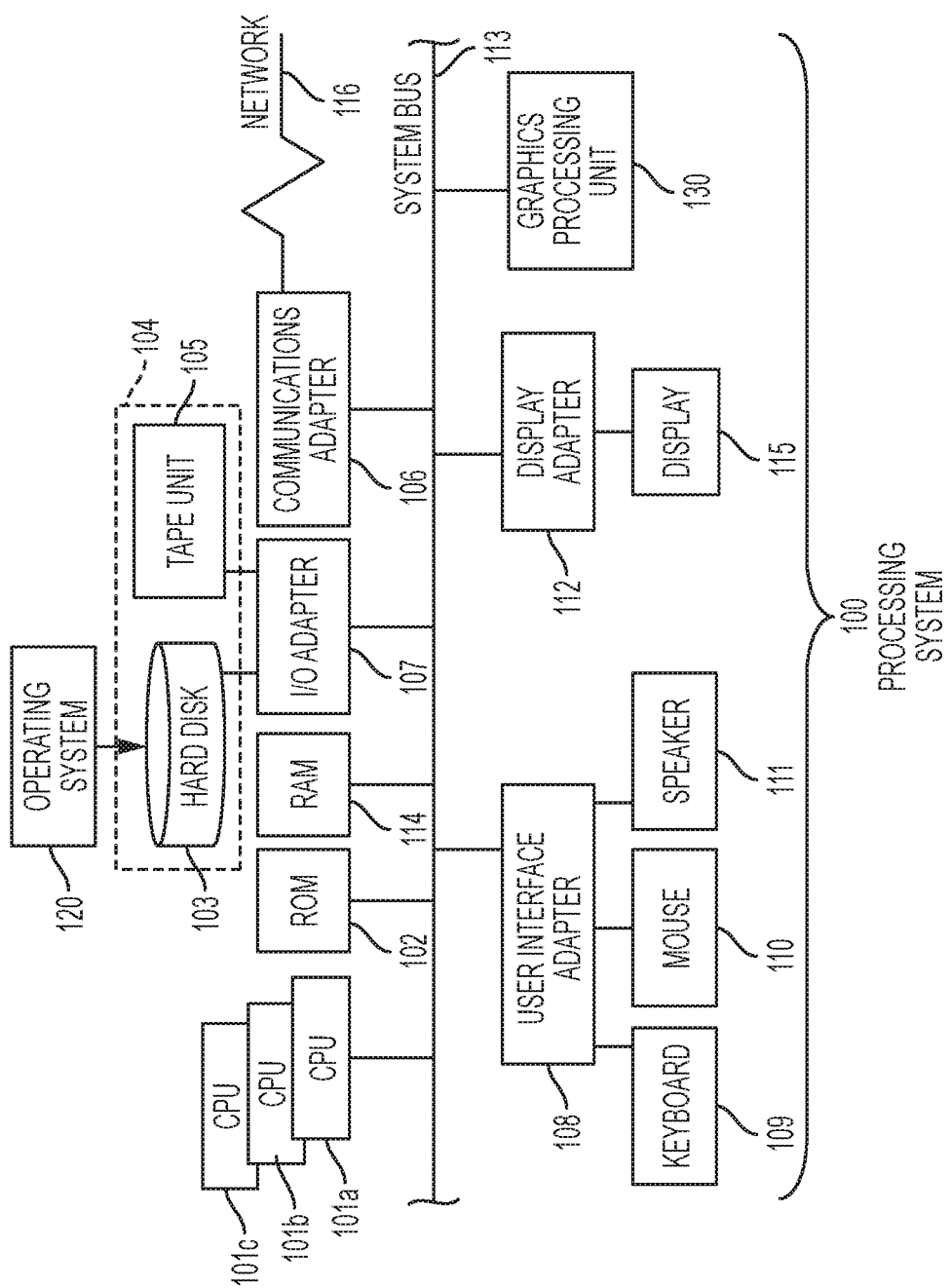
FIG. 3 is a block diagram illustrating one example of a processing system for practice of the teachings herein.

Referring to FIG. 3, there is shown a processing system 100 for implementing the teachings herein according to one or more embodiments. The system 100 has one or more central processing units (processors) 101*a*, 101*b*, 101*c*, etc. (collectively or generically referred to as processor(s) 101). In one embodiment, each processor 101 may include a reduced instruction set computer (RISC) microprocessor. Processors 101 are coupled to system memory 114 and various other components via a system bus 113. Read only memory (ROM) 102 is coupled to the system bus 113 and may include a basic input/output system (BIOS), which controls certain basic functions of system 100.

FIG. 3 further depicts an input/output (I/O) adapter 107 and a network adapter 106 coupled to the system bus 113. I/O adapter 107 may be a small computer system interface (SCSI) adapter that communicates with a hard disk 103 and/or tape storage drive 105 or any other similar component. I/O adapter 107, hard disk 103, and tape storage device 105 are collectively referred to herein as mass storage 104. Operating system 120 for execution on the processing system 100 may be stored in mass storage 104. A network adapter 106 interconnects bus 113 with an outside network 116 enabling data processing system 100 to communicate with other such systems. A screen (e.g., a display monitor) 115 is connected to system bus 113 by display adaptor 112, which may include a graphics adapter to improve the performance of graphics intensive applications and a video controller. In one embodiment, adapters 107, 106, and 112 may be connected to one or more I/O busses that are connected to system bus 113 via an intermediate bus bridge (not shown). Suitable I/O buses for connecting peripheral devices such as hard disk controllers, network adapters, and graphics adapters typically include common protocols, such as the Peripheral Component Interconnect (PCI). Additional input/output devices are shown as connected to system bus 113 via user interface adapter 108 and display adapter 112. A keyboard 109, mouse 110, and speaker 111 all interconnected to bus 113 via user interface adapter 108, which may include, for example, a Super I/O chip integrating multiple device adapters into a single integrated circuit.

In exemplary embodiments, the processing system 100 includes a graphics processing unit 130. Graphics processing unit 130 is a specialized electronic circuit designed to manipulate and alter memory to accelerate the creation of images in a frame buffer intended for output to a display. In general, graphics processing unit 130 is very efficient at manipulating computer graphics and image processing, and has a highly parallel structure that makes it more effective than general-purpose CPUs for algorithms where processing of large blocks of data is done in parallel.

Thus, as configured in FIG. 3, the system 100 includes processing capability in the form of processors 101, storage capability including system memory 114 and mass storage 104, input means such as keyboard 109 and mouse 110, and output capability including speaker 111 and display 115. In one embodiment, a portion of system memory 114 and mass storage 104 collectively store an operating system to coordinate the functions of the various components shown in FIG. 3.

In accordance with one or more embodiments of the present invention, methods, systems, and computer program products are disclosed for identifying personalized time-varying predictive patterns of risk factors to one or more particular target events for a specific individual patient having certain disease conditions.

One or more embodiments of the present invention allow a health care provider to proactively monitor the progress or functional change over time of a certain disease that is afflicting a particular individual patient. Then, using that information regarding the physiopathology of the disease within a particular patient, the health care provider can develop a patient-specific treatment, intervention and/or engagement plan. The embodiments disclosed may identify the personalized risk factor of a particular individual patient to various target events such as, for example and without limitation, the onset of a particular disease within the patient, the mortality of the patient from that disease, and the need for a hospital stay of that patient due to the disease. That is, the identified predictive pattern(s) for a particular individual patient indicates the relative importance of the various different risk factors for predicting the occurrence of a certain target event (e.g., the risk factor being the likelihood of mortality from a particular disease).

In addition, one or more embodiments of the present invention may also assist the health care provider in improving treatment of a specific individual patient due to the fact that the identified risk factors take into account the time-varying physiopathology nature of the disease that is afflicting that specific individual patient.

One or more embodiments of the present invention help to identify personalized time-varying predictive patterns of risk factors for individuals having various certain diseases by leveraging upon similarities of different patients at different time stamps (i.e., at different points in time during the progression of the disease from onset through cure or mortality) and also by leveraging upon risk factor assessment at the different time stamps.

Accordingly, embodiments of the present invention provide a patient-centric volume-to-value paradigm shift in the health care industry.

Figure 4:
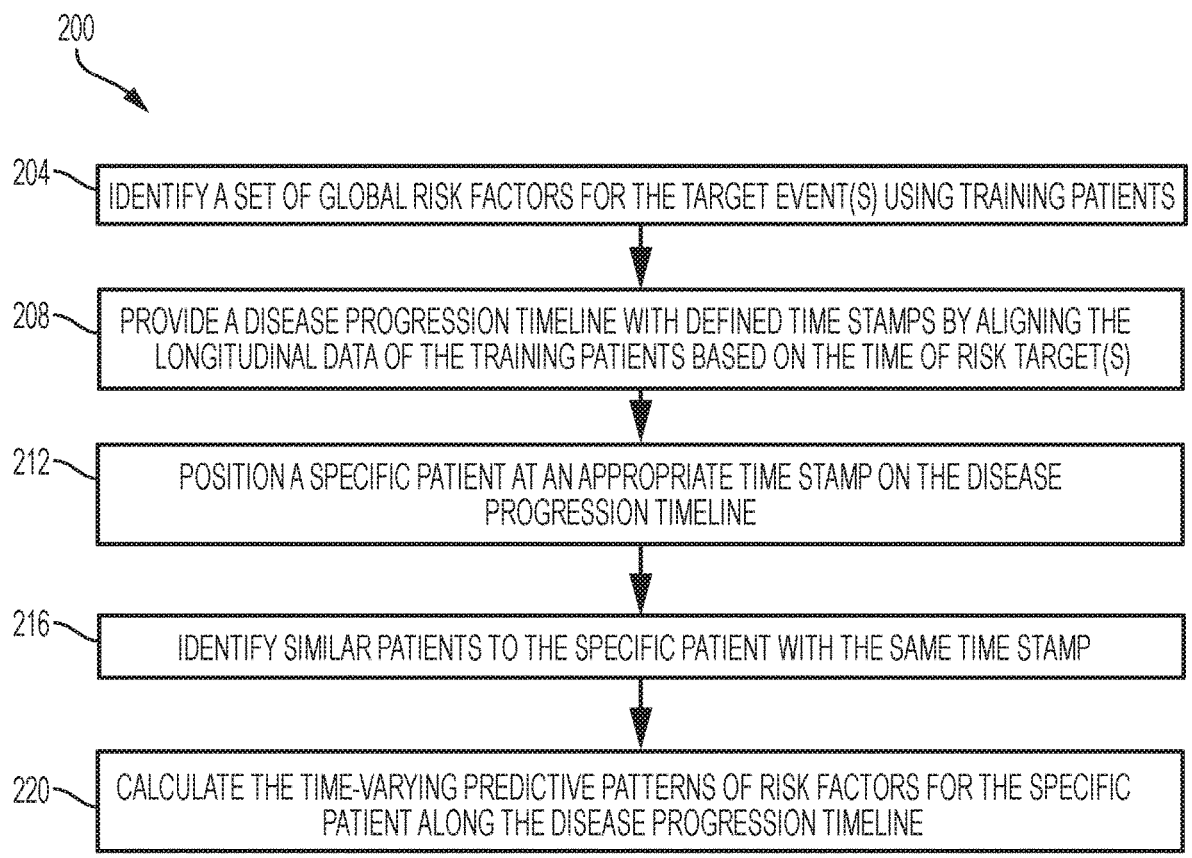
FIG. 4 is a flow diagram of a method for identifying personalized time-varying predictive patterns of risk factors for humans having various diseases in accordance with one or more embodiments of the present invention.

With reference now to FIG. 4, a flow diagram illustrates a method 200 according to one or more embodiments of the present invention for identifying a personalized time-varying predictive pattern of risk factors to one or more target events for a specific individual patient having certain diseases. In various embodiments, the method may be executed a number of times, each time for a different individual with the same or different diseases.

In one or more embodiments of the present invention, the method 200 may be embodied in software that is executed by computer elements located within a network that may reside in the cloud, such as the cloud computing environment 50 described hereinabove and illustrated in FIGS. 1 and 2. In other embodiments, the computer elements may reside on a computer system or processing system, such as the processing system 100 described hereinabove and illustrated in FIG. 3.

In block 204, a set of global risk factors are identified for one or more target events using the historical data gathered and stored from prior patients. This data may be referred to as training data and the patients may be referred to as training patients. Exemplary target events may include, for example and without limitation, the onset of a particular disease within the patient, the mortality of the patient, and the need for hospitalization of that patient.

Figure 5A:
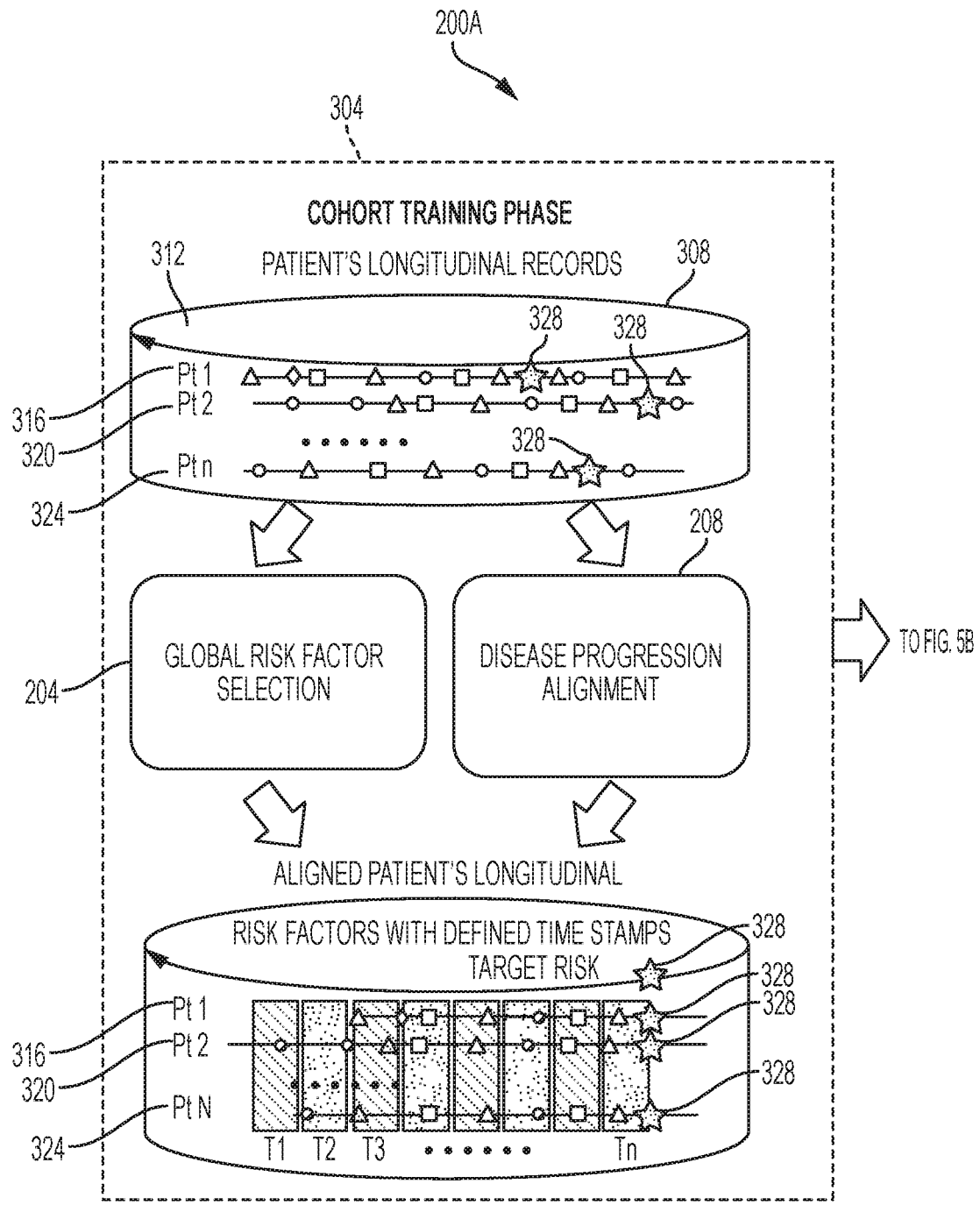
FIGS. 5A and 5B are flow diagrams illustrating in more detail the various phases and operations in the method of the flow diagram of FIG. 4 in accordance with one or more embodiments of the present invention.
Figure 5B:
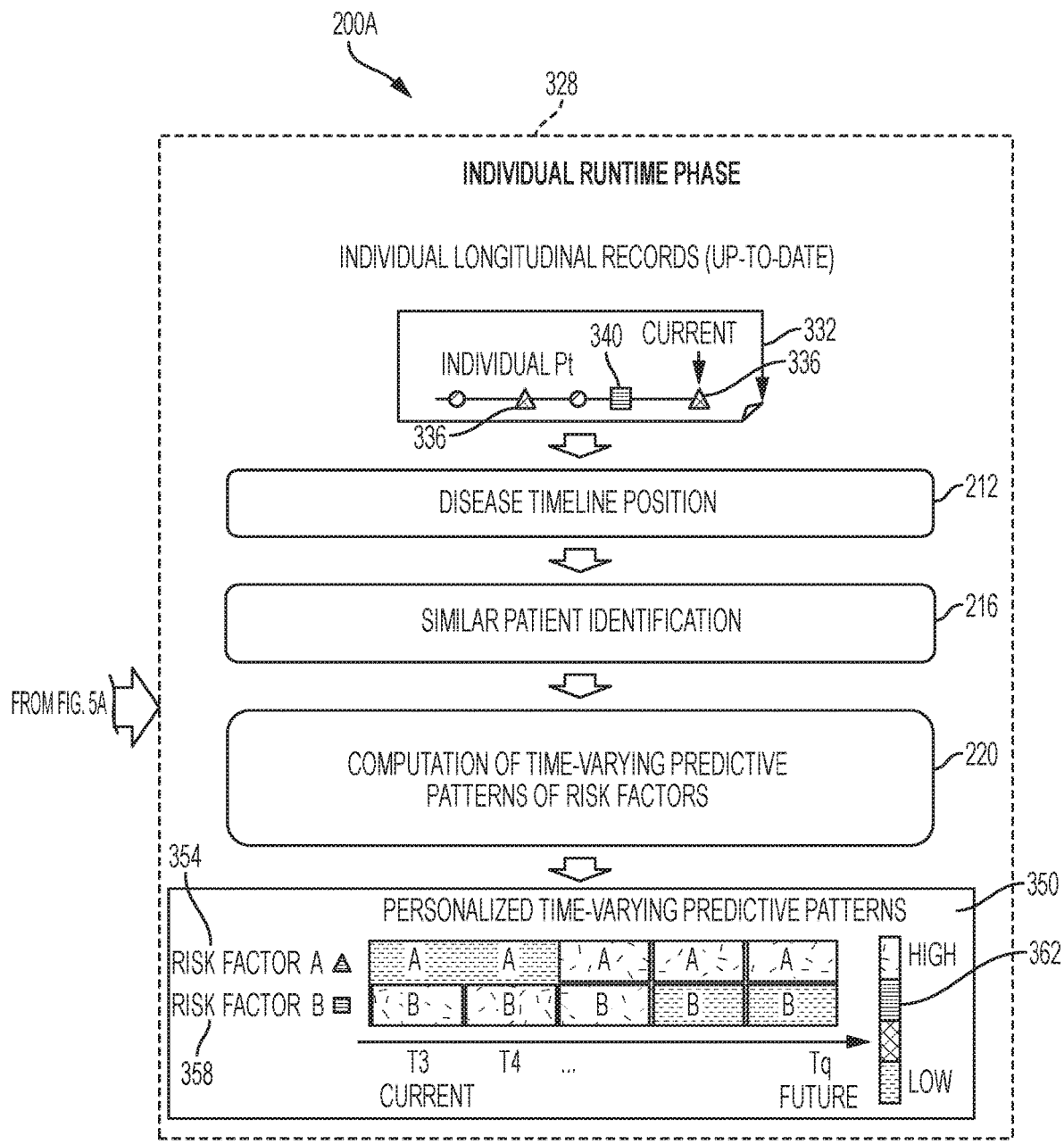
Figure 6:
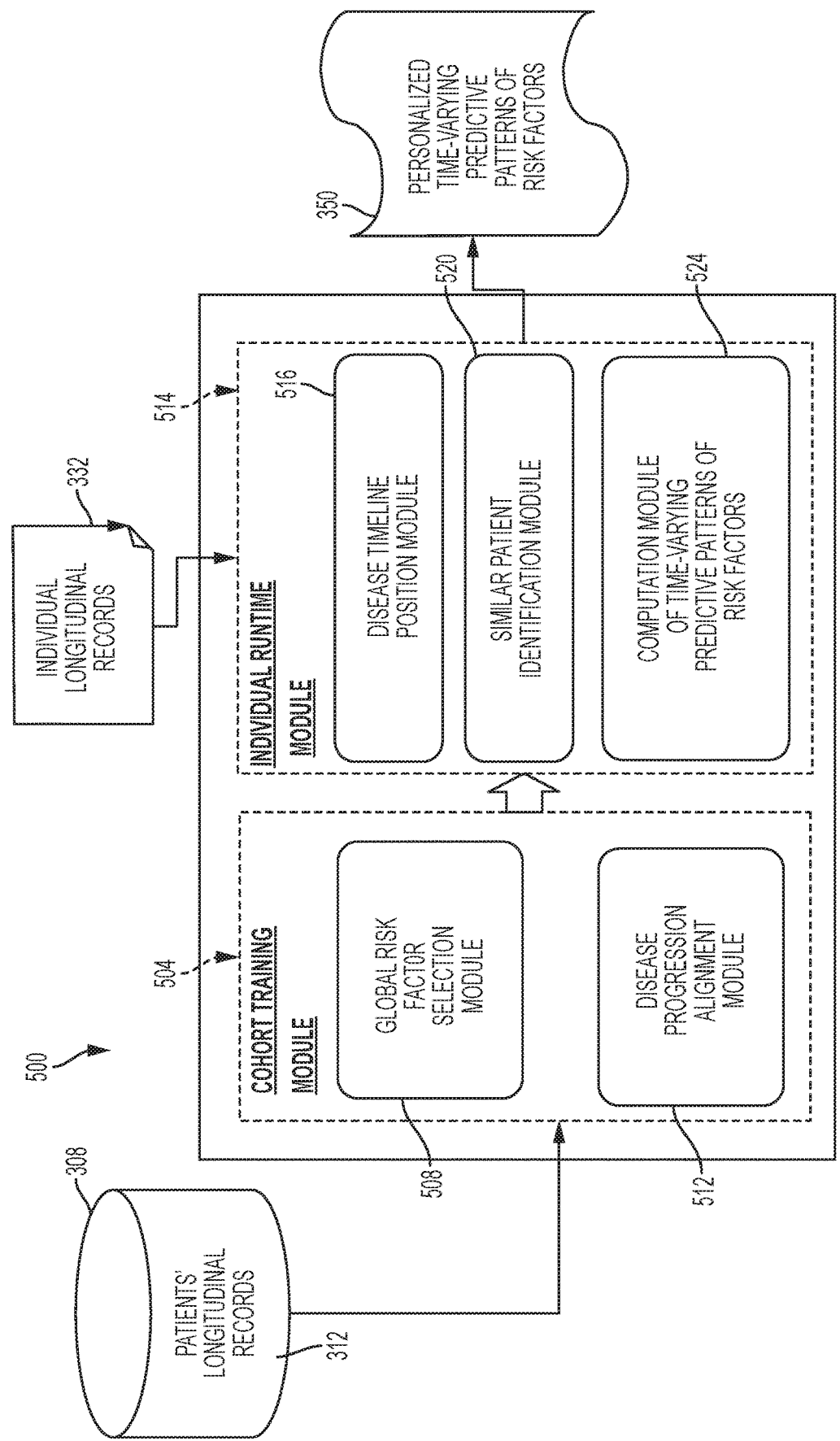
FIG. 6 is a block diagram illustrating the various components in a system configured to carry out the method of the flow diagrams of FIGS. 4, 5A and 5B in accordance with one or more embodiments of the present invention.

Reference is also now made to FIGS. 5A, 5B and 6. FIGS. 5A and 5B are flow diagrams illustrating in more detail the phases and the operations in the method 200 of the flow diagram of FIG. 4 in accordance with one or more embodiments of the present invention. As shown in FIGS. 5A and 5B, the method 200 of FIG. 4 is referred to as the method 200A. FIG. 6 is a block diagram illustrating the various components of a system 500 configured to carry out the method 200, 200A of the flow diagrams of FIGS. 4, 5A and 5B in accordance with one or more embodiments of the present invention.

Block 204 may be carried out during a cohort training phase 304 (FIG. 5A) by a cohort training module 504 (FIG. 6). That is, prior to one or more embodiments of the present invention being utilized on a particular person with a specific disease, a first portion of the method 200, 200A may involve building a database comprising stored data, which includes historical information about a first number of people or patients (i.e., "cohorts") all having (or who have had) a first particular disease (e.g., heart failure), a second number of people or patients all having or who have had a second particular disease (e.g., coronary artery disease), and so forth. In other embodiments, this database may have already been built or populated with the relevant data and is thus available for use in the method 200, 200A.

The database can be populated in the above-described manner as desired with as many diseases and with data relating to a number of individual groups of persons each having a particular one of the diseases. The database of historical or training diseases and patient data or information can be built or populated when embodiments of the present invention are first implemented. Also, in one or more embodiments, as data becomes available over time for additional people with the same disease, such data can be integrated into or added to the database, thereby making the database up to date and relatively more robust, such that now embodiments of the present invention reflect the most modern techniques and corresponding results for treating various diseases.

Nevertheless, as will be seen in more detail hereinafter, training data involving a plurality of people having certain diseases (e.g., heart failure) is required to allow embodiments of the present invention to run an iteration involving a new patient that has that certain disease. This way, personalized time-varying predictive patterns of risk factors may be identified with respect to that new patient.

It should be noted that embodiments of the present invention are not limited to a particular disease, such as heart disease. Instead, heart disease is merely an exemplary type of disease used in embodiments. Any type of disease may be used with embodiments of the present invention. Also, embodiments may identify similar patients with slightly different disease conditions, and can assess patient health status as a holistic picture and does not need to necessarily focus on a particular disease. For example, the target event may be the hospitalization of a patient, which can be triggered by one disease of an interaction of different diseases. In most situations, the latter situation exists; that is, a patient's health decline is introduced by many different comorbidities.

The database may comprise a type of memory storage device 308 (FIGS. 5A, 6), such as one associated with the cloud computing environment 50 described hereinabove and illustrated in FIGS. 1 and 2, or one associated with the processing system 100 described hereinabove and illustrated in FIG. 3. The database 308 may store data relating to a number of patients, wherein the stored data may be referred to as the training or historical patients' longitudinal records 312. These longitudinal records 312 typically involve various types of data generated over a period of time, as illustrated in FIG. 5A. There, the longitudinal data, or data generated over time, for each one of the historical or training patients, is indicated by a line 316 labeled "Pt. 1" for patient number 1, by a line 320 labeled "Pt. 2" for patient number 2, and so forth until the line 324 for the last patient, "Pt. n." There is no set or fixed number of training patients required for embodiments of the present invention. However, embodiments contemplate that as the number of training patients is made larger, a relatively better cross section of data may be obtained for people having certain disease(s) and for the associated treatment of each of these patients by health care providers.

Each patient's longitudinal record 316, 320, 324 in FIG. 5A is illustrated as having various symbols or labels at different points in time (i.e., "time stamps") along each line 316, 320, 324. For example, the star symbol 328 on each of the lines 316, 320, 324 may indicate the time that a certain target event occurred for that particular training patient. As mentioned hereinabove, exemplary target events may include, for example and without limitation, the onset of a particular disease within the patient, the mortality of the patient, and the need for hospitalization of that patient. Thus, in FIG. 5A, each star symbol 328 may represent the time that each training patient with that particular disease required a hospitalization stay. That is, the star symbol 328 for each longitudinal record 316, 320, 324 may be a case record, which is a type of record in which a certain target event occurred—in this example a required hospitalization stay. In the alternative, the star symbol 328 may indicate the non-occurrence of a certain target event when instead the occurrence of that target event was anticipated to occur (e.g., the progression of a particular disease to a certain stage). In this example, the star symbol 328 may be referred to as a control record.

The individual training patents' longitudinal records 316, 320, 324 may also include other symbols (e.g., triangles, diamonds, squares, circles, etc.) located along the timelines at particular time stamps. These different symbols represent the occurrence of various different events which may be common for a patient with a particular disease (e.g., seeing the health care provider at certain time intervals, having labs performed at certain time intervals, etc.). Also, it is now common for patients' records to be embodied in electronic form, which allows different doctors' offices at different locations to more easily access these records using computers. This type of shared data or information may, for example, be shared between doctors in different offices in the same city, be shared across a regional health care system (e.g., within a state or multiple nearby states, or even shared across a nationwide network, such as the national Veterans' Affairs ("VA") health care system.

These electronic medical records ("EMRs") typically include data or information relating to the occurrence or non-occurrence of health care treatment events that may be common to a particular type of disease or may be common to the general practice of health care by health care providers. The data or information in the EMRs may include data or information, for example and without limitation, relating to any diagnosis given, labs or lab work performed, medications prescribed and/or taken, patient vital signs (e.g., blood pressure, pulse, etc.), symptom notes, etc. The data or information may also not relate to EMRs and, as such, may include data such as, for example and without limitation, activity and/or behavior sensor data, questionnaire data, etc.

It should be noted that these symbols are shown in FIG. 5A for illustrative purposes only to demonstrate the typical existence of differences between types of data within the longitudinal records of patients. If embodiments of the invention include a visual display unit, such as a computer video screen, then the individual training patents' longitudinal records 316, 320, 324 may be shown on the video screen in the manner given in FIG. 5A, including with the various symbols. This way, the user can easily see the types of data and the time stamps associated with the data relating to a training patient.

Once a database 308 is available that contains the longitudinal historical records 312 of a number of patients that have or have had certain diseases, block 204 in the method 200, 200A of the flow diagram of FIGS. 4, 5A and 5B may be carried out in which a set of global risk factors for one or more target events are identified using the aforementioned training data within the database 308. Block 204 may be carried out by the module 508 within the system 500 of FIG. 6. This module 508, and any other modules in the system 500, may comprise or be embodied in software executed by a processor or other computing device (FIGS. 1-3). In various embodiments of the present invention, known feature selection algorithms may be used to identify the global risk factors for the desired target events from among the stored training data.

In block 208 (FIGS. 4, 5A) and in a module 512 (FIG. 6), a disease progression timeline with defined time stamps is provided or determined. The timeline may be determined, for example, by aligning the longitudinal data of the training patients based on the point in time (time stamp) of the occurrence of one of the target events. Block 208 and module 512 are shown in both FIGS. 5A and 6.

More specifically, an exemplary risk factor of a target event 328 (e.g., the start of a hospitalization stay) for each one of the individual training patents' longitudinal records 316, 320, 324 may be shown as being aligned in time with one another (e.g., all risk targets 328 aligned vertically), as best seen in FIG. 5A. Thus, each training patient's longitudinal record or timeline 316, 320, 324 may need to be shifted in time, as shown in FIG. 5A, to properly align (vertically as shown in FIG. 5A) all of the desired risk targets (e.g., risk targets 328) in time with one another, as given by the time stamps associated with the desired risk target for each longitudinal record 316, 320, 324.

This resulting alignment of risk target data gives the health care provider information regarding the differing amounts of time (as between the training patients) that it took to reach the desired target event being investigated from a certain starting point, e.g., a disease starting point or onset in time. The disease progression timeline may generate the relative number of time stamps to the risk target event that are relevant to the investigation by the health care provider. The number of defined time stamps may be indicted by q. In FIG. 5A, the "Pt. 2" longitudinal record 320 started the earliest in time (as compared to the time stamp of the risk target event 328), while the "Pt. 1" longitudinal record 316 started the latest in time (as compared to the time stamp of the risk target event 328).

Note that blocks 204 and 208 need not be performed sequentially in time. Instead, embodiments of the present invention contemplate that these two operations may be performed at the same time (i.e., in parallel), as illustrated in FIGS. 5A and 6. This is because neither block 204 nor block 208 requires an output from the other of block 204 or block 208 before that block/operation can be performed.

After block 208, the set of global risk factors have been identified and a disease progression timeline has been provided. Both of blocks 204, 208 were performed in a cohort training phase 304 in the method 200, 200A of FIG. 5A, and by a cohort training module 504 in the system of FIG. 6. The method 200, 200A of FIGS. 4, 5A and 5B may now transition to an individual runtime phase 328 (FIG. 5B) and an individual runtime module 514 (FIG. 6). That is, the database 308 has been created with historical or training data regarding a number of patients having a specific disease, and now the method 200, 200A can transition to a phase where a new or target patient can have his/her personalized time-varying predictive patterns of risk factors calculated, computed, determined or otherwise identified.

Prior to the performance of a block 212 in the method 200, 200A, embodiments of the present invention include the provision of the longitudinal records 332 of a "new" or "target" patient to be used by the remaining operations in the method 200, 200A. That is, the new or target patient is one that is not an historical or training patient whose records 312 were stored in the database 308 and utilized by the aforementioned blocks 204, 208 in the method 200, 200A. Instead, the new or target patient is one whose longitudinal records 332 are being used for the first time by embodiments of the present invention. That is, the new or target patient is one who has never had any data relating to a particular disease entered into the database 308 before. Thus, the patient himself/herself may be new to the database 308, or the patient may not be new to the database 308 but the disease that the patient now has may be new to the database 308. The longitudinal records 332 of the new or target patient may include the same historical components as in the longitudinal records 312 of the training patients. Also, the longitudinal records 332 of the new or target patient are desirably up-to-date records.

For example, as shown in FIG. 5B, the longitudinal record 332 of the new or target patient may include one or more types of symbols 336, 340, where each symbol 336, 340 may represent the occurrence at a certain time stamp or point in time of a certain target event relating to that patient. As example, the symbol 336 may represent a needed hospitalization stay, while the symbol 340 may represent having lab work performed (e.g., blood drawn from that new patient and analyzed). The longitudinal record 332 may be up-to-date in that the right most symbol 336 on the record line 332 is shown as being labeled as "current."

In block 212 (FIGS. 4, 5B) and in a module 516 (FIG. 6), the new or target individual patient may be positioned at an appropriate time stamp, or point in time, on the disease progression timeline that was provided in block 208 and discussed hereinabove. Specifically, the target individual patient may be positioned at a time stamp (i) as compared to the aligned training patients' longitudinal records 312 (i.e., the disease progression timeline) from block 208. For example, the new or target patient may have a time stamp of the start of a hospital stay 328 aligned vertically in time with the other similar risk factors 328 involving the hospitalization stay target event, as was shown in FIG. 5A.

Block 212 may include two scenarios. A first scenario is one in which the risk target of the new or target individual patient is assessed after a certain time following an onset event (e.g., the risk of bleeding [risk target] after three (3) months [a certain time] following cardiovascular surgery [onset event]). In this scenario, the individual patient can be positioned to the time stamp (i) according to the time distance to the onset event.

A second scenario is one in which the risk target is assessed without an obvious onset event (e.g., the risk of heart failure in a year). In this scenario, the similarity scores of the target individual to the training patients at q different time stamps need to be calculated; the time stamp (i) with the best similarity score is selected to position the target individual patient on the disease progression timeline. The similarity scores can be computed by known algorithms or methods, such as for example and without limitation, Euclidean, Mahalanobis, Manhattan distance, or any type of distance or similarity method.

Block 216 (FIGS. 4, 5B) and a module 520 (FIG. 6) comprises identifying similar training patients to the new or target individual patient with the same time stamp. Specifically, similar training patients to the new or target individual patient may be identified from training cohort data stored in the database 308 based on records at the current time stamp and all available prior time stamps. The training patients utilized may be both case and control patients, with a case patient being one having had a particular disease (e.g., heart failure), and with a control patient being one that did not have that particular disease (e.g., again, heart failure). The similarity measures may, for example, comprise rule based constraints, target independent measures such as Euclidean, Mahalanobis, Manhattan distance, etc., or may comprise target specific (metric learning) measures that are trained on a similar training patient data set.

Block 220 (FIGS. 4, 5B) and a module 524 (FIG. 6) comprises the computation or identification of the time-varying predictive patterns of risk factors for the specific new or target individual patient. The predictive score of each risk factor may be calculated at q time stamps using longitudinal records from similar training patients. The predictive score can be measured by information gain, correlation, etc. The risk factors and their associated scores can be computed using a number of feature selection algorithms including, but not limited to, filter, wrapper and embedded methods in the context of a cross validation network. Block 220 results in the identification (e.g., calculation, computation, determination, etc.) of the patient-specific, time-varying predictive patterns of risk factors 350.

In FIG. 5B, two separate risk factors are shown for the individual target patient over a time period of from T3, T4, through Tq in the future. "Risk factor A" 354, which corresponds to the triangle symbol 336 of the line 332 (i.e., a needed hospitalization stay), and "Risk factor B" 358, which corresponds to the square symbol 340 of the line 332 (i.e., having lab work performed) are shown in FIG. 5B in the box labeled "Personalized Time-Varying Predictive Patterns" 350. The predictive score of the risk factor in the time period shown can be depicted quantitatively in FIG. 5B using a scale 362 which shows, at one end, a relatively high score and at the other end, a relatively low score, with two intermediate levels in between. This quantitative depiction can be illustrated with respect to "Risk factor A" 354 and "Risk factor B" 358, as seen in FIG. 5B.

An exemplary use case scenario for one or more embodiments of the present invention follows. John Doe and John Roe are two patients of Dr. Smith. Both John Doe and John Roe feel fatigue and shortness of breath after walking a block, but they have different measures of left ventricular ejection fraction (LVEF). Dr. Smith wants to use routine lab tests periodically to track and assess their risk of onset of heart failure (HF).

Using the teachings of the embodiments disclosed herein, the current (i.e., up-to-date) longitudinal record or profile for each of John Doe and John Roe are compared to the longitudinal records of a number of training patients in a heart failure database. Based on the historical longitudinal records in the training database, it can be determined, for example, that John Doe and John Roe are both likely to develop heart failure in six months.

Then, based on predictive score assessment of lab test results (e.g., blood testing) from similar training patients, Dr. Smith may identify that the predictive patterns of a particular risk factor, for example, the labs, will be different as between John Doe and John Roe over the next six months. With this information, Dr. Smith can do several things: 1) proactively track different labs for John Doe and John Roe; 2) personalize heart failure risk prediction at different time stamps using the labs; and/or 3) develop patient-specific, time-sensitive intervention/treatment plans for both John Doe and John Roe.

One or more embodiments of the present invention allows health care providers to proactively monitor the disease progress for a particular individual patient, predict the personalized risk of a patient to a target event, and develop a patient-specific treatment, intervention or engagement plan.

Also, one or more embodiments of the present invention position an individual patient on the disease progression timeline at a particular time stamp to facilitate the investigation of risk factors at different time points. Also, a group of similar patients (both cases and controls) with the same time stamp may be identified for the individual patient using patient similarity. Further, the personalized predictive patterns of risk factors are identified for the target individual.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

As used herein, the articles "a" and "an" preceding an element or component are intended to be nonrestrictive regarding the number of instances (i.e., occurrences) of the element or component. Therefore, "a" or "an" should be read to include one or at least one, and the singular word form of the element or component also includes the plural unless the number is obviously meant to be singular.

As used herein, the terms "invention" or "present invention" are non-limiting terms and not intended to refer to any single aspect of the particular invention but encompass all possible aspects as described in the specification and the claims.

As used herein, the term "about" modifying the quantity of an ingredient, component, or reactant of the invention employed refers to variation in the numerical quantity that can occur, for example, through typical measuring and liquid handling procedures used for making concentrates or solutions. Furthermore, variation can occur from inadvertent error in measuring procedures, differences in the manufacture, source, or purity of the ingredients employed to make the compositions or carry out the methods, and the like. In one aspect, the term "about" means within 10% of the reported numerical value. In another aspect, the term "about" means within 5% of the reported numerical value.

Yet, in another aspect, the term "about" means within 10, 9, 8, 7, 6, 5, 4, 3, 2, or 1% of the reported numerical value.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method comprising:
    identifying, by a processor, a set of global risk factors for a target event using training patients;
    providing, by the processor, a disease progression timeline with defined time stamps by aligning longitudinal data of the training patients based on the defined time stamp of risk targets, wherein the longitudinal data of the training patients is obtained from the medical records of the training patients, and wherein the target event is a hospitalization of the target patient triggered by one disease of an interaction of different diseases;
    positioning, by the processor, a target patient at one of the defined time stamps on the disease progression timeline, wherein a number of defined time stamps associated with the target event is based at least in part on an investigation of a health care provider;
    identifying, by the processor, at least one of the training patients similar to the target patient with the same one of the defined time stamps on the disease progression timeline;
    calculating, by the processor, a respective time-varying predictive pattern of at least a portion of the set of global risk factors for the target patient along the disease progression timeline; and
    displaying, by the processor, respective rows of the time-varying predicative patterns for the target patient, wherein the rows are segmented based on time intervals from a current time interval to a future time interval, and wherein each segment describes a time-based risk score for the target patient via a visual pattern.

2. The computer-implemented method of claim 1 wherein the calculated time-varying predictive pattern of at least a portion of the set of global risk factors comprises a calculated time-varying predictive pattern of multiple risk factors within the set of global risk factors.

3. The computer-implemented method of claim 1 wherein the target event comprises an event related to certain diseases that afflicts humans.

4. The computer-implemented method of claim 1 wherein positioning, by the processor, a target patient at one of the defined time stamps on the disease progression timeline comprises assessing the risk target of the target patient after a certain time following an onset event and positioning the target to the one of the defined time stamps according to an amount of time to the onset event.

5. The computer-implemented method of claim 1 wherein positioning, by the processor, a target patient at one of the defined time stamps on the disease progression timeline comprises assessing the risk target of the target patient with no occurrence of an onset event.

6. The computer-implemented method of claim 5 wherein assessing the risk target of the target patient with no occurrence of an onset event comprises calculating similarity scores of the target patient to the training patients at a number of different time stamps, wherein one of the different time stamps is selected to position the target patient on the disease progression timeline.

7. The computer-implemented method of claim 6 wherein the similarity scores are calculated by a distance or similarity method.

8. A system comprising:
    a processor in communication with one or more types of memory, the processor configured to:
    identify a set of global risk factors for a target event using training patients;
    provide a disease progression timeline with defined time stamps by aligning longitudinal data of the training patients based on the defined time stamp of risk targets, wherein the longitudinal data of the training patients is obtained from the medical records of the training patients, and wherein the target event is a hospitalization of the target patient triggered by one disease of an interaction of different diseases;
    position a target patient at one of the defined time stamps on the disease progression timeline, wherein a number of defined time stamps associated with the target event is based at least in part on an investigation of a health care provider;
    identify at least one of the training patients similar to the target patient with the same one of the defined time stamps on the disease progression timeline; and
    calculate a respective time-varying predictive pattern of at least a portion of the set of global risk factors for the target patient along the disease progression timeline; and
    displaying respective rows of the time-varying predicative patterns for the target patient, wherein the rows are segmented based on time intervals from a current time interval to a future time interval, and wherein each segment describes a time-based risk score for the target patient via a visual pattern.

9. The system of claim 8 wherein the processor configured to calculate a time-varying predictive pattern of at least a portion of the set of global risk factors comprises the processor configured to calculate a time-varying predictive pattern of multiple risk factors within the set of global risk factors.

10. The system of claim 8 wherein the target event comprises an event related to certain diseases that afflicts humans.

11. The system of claim 8 wherein the processor being configured to position a target patient at one of the defined time stamps on the disease progression timeline comprises the processor being configured to assess the risk target of the target patient after a certain time following an onset event and position the target to the one of the defined time stamps according to an amount of time to the onset event.

12. The system of claim 8 wherein the processor being configured to position a target patient at one of the defined time stamps on the disease progression timeline comprises the processor being configured to assess the risk target of the target patient with no occurrence of an onset event.

13. The system of claim 12 wherein the processor being configured to assess the risk target of the target patient with no occurrence of an onset event comprises the processor being configured to calculate similarity scores of the target patient to the training patients at a number of different time stamps and to select one of the different time stamps to position the target patient on the disease progression timeline.

14. The system of claim 13 wherein the similarity scores are calculated by a distance or similarity method.

15. A computer program product comprising:
a non-transitory storage medium readable by a processing circuit and storing instructions for execution by the processing circuit for performing a method comprising:
identifying, by a processor, a set of global risk factors for a target event using training patients;
providing, by the processor, a disease progression timeline with defined time stamps by aligning longitudinal data of the training patients based on the defined time stamp of risk targets, wherein the longitudinal data of the training patients is obtained from the medical records of the training patients, and wherein the target event is a hospitalization of the target patient triggered by one disease of an interaction of different diseases;
positioning, by the processor, a target patient at one of the defined time stamps on the disease progression timeline, wherein a number of defined time stamps associated with the target event is based at least in part on an investigation of a health care provider;
identifying, by the processor, at least one of the training patients similar to the target patient with the same one of the defined time stamps on the disease progression timeline; and
calculating, by the processor, a time-varying predictive pattern of at least a portion of the global set of risk factors for the target patient along the disease progression timeline; and
displaying, by the processor, respective rows of the time-varying predicative patterns for the target patient, wherein the rows are segmented based on time intervals from a current time interval to a future time interval, and wherein each segment describes a time-based risk score for the target patient via a visual pattern.

16. The computer program product of claim 15 wherein the calculated time-varying predictive pattern of at least a portion of the global set of risk factors comprises a calculated time-varying predictive pattern of multiple risk factors within the set of global risk factors.

17. The computer program product of claim 15 wherein the target event comprises an event related to certain diseases that afflicts humans.

18. The computer program product of claim 15 wherein positioning, by the processor, a target patient at one of the defined time stamps on the disease progression timeline comprises assessing the risk target of the target patient after a certain time following an onset event and positioning the target to the one of the defined time stamps according to an amount of time to the onset event.

19. The computer program product of claim 15 wherein positioning, by the processor, a target patient at one of the defined time stamps on the disease progression timeline comprises assessing the risk target of the target patient with no occurrence of an onset event.

20. The computer program product of claim 19 wherein assessing the risk target of the target patient with no occurrence of an onset event comprises calculating similarity scores of the target patient to the training patients at a number of different time stamps, wherein one of the different time stamps is selected to position the target patient on the disease progression timeline.

* * * * *